(12) United States Patent
Stepanski et al.

(10) Patent No.: US 10,745,332 B2
(45) Date of Patent: Aug. 18, 2020

(54) PROCESS FOR PURIFYING A CRUDE COMPOSITION INCLUDING A MONOTERPENE COMPOUND, SUCH AS A MONOCYCLIC MONOTERPENE ALCOHOL, BY LAYER MELT CRYSTALLIZATION

(71) Applicant: Sulzer Management AG, Winterthur (CH)

(72) Inventors: Manfred Stepanski, Buchs (CH); Florian Lippuner, Gams (CH); Hans-Peter Brack, Herrliberg (CH)

(73) Assignee: SULZER MANAGEMENT AG, Winterthur (CH)

( * ) Notice: Subject to any disclaimer, the term of this patent is extended or adjusted under 35 U.S.C. 154(b) by 0 days.

(21) Appl. No.: 16/604,642

(22) PCT Filed: Apr. 13, 2018

(86) PCT No.: PCT/EP2018/059566
§ 371 (c)(1),
(2) Date: Oct. 11, 2019

(87) PCT Pub. No.: WO2018/189386
PCT Pub. Date: Oct. 18, 2018

(65) Prior Publication Data
US 2020/0071249 A1    Mar. 5, 2020

(30) Foreign Application Priority Data
Apr. 13, 2017  (EP) ..................................... 17166535

(51) Int. Cl.
*C07C 29/00* (2006.01)
*C07C 29/78* (2006.01)

(52) U.S. Cl.
CPC .......... *C07C 29/78* (2013.01); *C07C 2601/14* (2017.05)

(58) Field of Classification Search
CPC .................................................... C07C 29/78
See application file for complete search history.

(56) References Cited

U.S. PATENT DOCUMENTS

| 5,773,410 A | 6/1998 | Yamamoto |
| 7,868,211 B2 | 1/2011 | Rauls et al. |
| 2013/0046118 A1 | 2/2013 | Heydrich et al. |

FOREIGN PATENT DOCUMENTS

EP    0 694 514 A2    1/1996

OTHER PUBLICATIONS

Felix Eisenbart et al: "Solvent-aided layer crystallization of glycerol—Post treatment and the influence of agitation", Chemical Engineering and Technology, vol. 39, No. 7, 2016, pp. 1251-1256, Weinheim, ISSN: 0930-7516.

Extended European Search Report dated Sep. 28, 2017 in corresponding European Patent Application No. 17166535.9, filed Apr. 13, 2017.

International Preliminary Report on Patentability and Written Opinion dated Oct. 15, 2019 in corresponding International Patent Application No. PCT/EP2018/059566, filed Apr. 13, 2018.

*Primary Examiner* — Sikarl A Witherspoon
(74) *Attorney, Agent, or Firm* — Global IP Counselors, LLP

(57) ABSTRACT

A process for purifying a crude composition includes a monoterpene compound selected from the group consisting of monocyclic monoterpene alcohols, monocyclic monoterpene ketones, bicyclic epoxy monoterpenes and mixtures of two or more of the aforementioned compounds, such as preferably a monocyclic monoterpene alcohol. The process comprises performing a layer crystallization with a melt of the crude composition, and the melt of the crude composition subjected to the layer crystallization includes oxygen-containing solvent in a concentration of 20 ppm to 2% by weight. The oxygen-containing solvent is selected from the group consisting of water, C1-6-alcohols, C1-6-carboxylic acids, C1-6-ketones, C1-6-aldehydes, C1-12-ethers, C1-12-esters and mixtures of two or more of the aforementioned solvents.

15 Claims, 1 Drawing Sheet

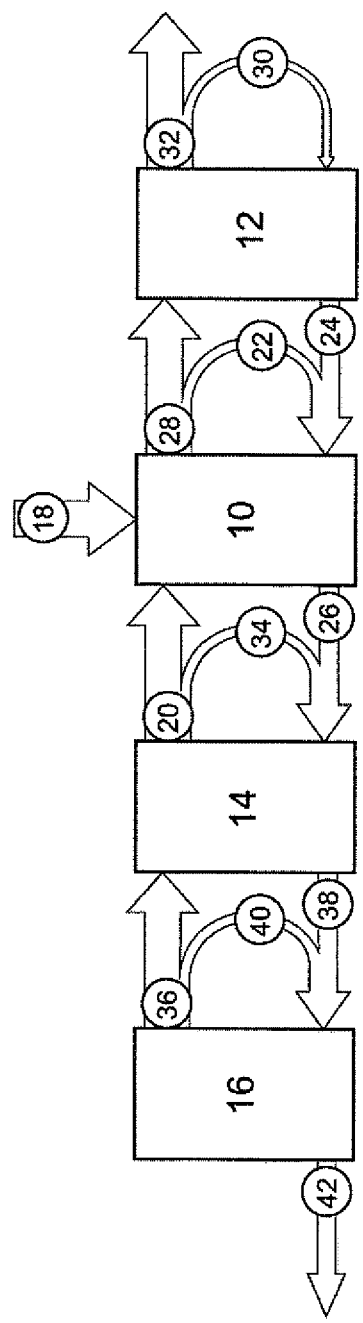

PROCESS FOR PURIFYING A CRUDE COMPOSITION INCLUDING A MONOTERPENE COMPOUND, SUCH AS A MONOCYCLIC MONOTERPENE ALCOHOL, BY LAYER MELT CRYSTALLIZATION

CROSS-REFERENCE TO RELATED APPLICATION

This application is a U.S. National Stage application of International Application No. PCT/EP2018/059566, filed Apr. 13, 2018, which claims priority to European Patent Application No. 17166535.9, filed Apr. 13, 2017, the contents of each of which are hereby incorporated herein by reference.

BACKGROUND

Field of the Invention

The present invention relates to a process for purifying a crude composition including a monoterpene compound selected from the group consisting of monocyclic monoterpene alcohols, monocyclic monoterpene ketones, bicyclic epoxy monoterpenes and mixtures of two or more of the aforementioned compounds, by layer melt crystallization, to an enriched composition of a monoterpene compound selected from the group consisting of monocyclic monoterpene alcohols, monocyclic monoterpene ketones, bicyclic epoxy monoterpenes and mixtures of two or more of the aforementioned compounds, to a racemic mixture of L-(−)-n-isopulegol and D-(−)-n-isopulegol and to the uses thereof.

Background

Monoterpene compounds, such as in particular monocyclic monoterpene alcohols, monocyclic monoterpene ketones and bicyclic epoxy monoterpenes, are an important group of naturally occurring chemical compounds and comprise for example isopulegol, 1,8-cineol, carvone, menthol, alpha-terpineol, thymol, carvacrol, piperitenol and perillyl alcohol. Thymol, for instance, is characterized by a high fungicide and bactericide effect and is used on account of these properties in tooth paste, mouthwash and similar products. Also carvacrol is a bactericide, whereas alpha-terpineol is a flavor, which is used for example in soaps and perfumes. As further example, 1,8-cineol, which is a bicyclic epoxy monoterpene and which naturally occurs as an ingredient of eucalyptus oil, is used in human and veterinary medicine as medicament as well as as flavoring agent in perfumes. Carvone, which is a monocyclic monoterpene ketone, is used in food applications and agriculture. As further example, menthol, i.e. 2-isopropyl-5-methylcyclohexanol, is an organic compound naturally occurring in corn mint, peppermint and other mint oils. Eight stereoisomers of menthol are known and some of these have disinfecting properties and are used for personal hygiene articles, for dental hygiene articles and for oral hygiene articles, whereas the stereoisomer (−)-menthol has a characteristic taste and is used as flavor in cigarettes, chewing gum and candies. Isopulegol, i.e. 2-isopropenyl-5-methylcyclohexanol, is very similar to menthol and differs from menthol in that it comprises instead of the saturated isopropyl group the unsaturated isopropenyl group. On account of this reason, isopulegol is often used as starting compound to prepare menthol by hydrogenating the isopulegol.

SUMMARY

As indicated above, each of the monoterpene compounds and particularly each of the monocyclic monoterpene alcohols exist in the form of several stereoisomers, whereas the characteristic properties of the monoterpene compounds, such as the monocyclic monoterpene alcohols, may significantly differ among the single stereoisomers. For example, menthol has three chirality centers, namely the carbon atom of the cyclohexyl ring bonded to the hydroxyl group, the carbon atom of the cyclohexyl ring bonded to the isopropyl group and the carbon atom of the cyclohexyl ring bonded to the methyl group. On account of this reason, there exist eight stereoisomers of menthol, namely four diastereoisomers, which are menthol, isomenthol, neomenthol and neoisomenthol, and two enantiomers, namely the (+)- and (−)enantiomers, of each of these diastereoisomers. Only one of these eight stereoisomers, namely (−)-menthol, has the characteristic taste and flavor, for which menthol is known. Due to this, menthol has to be synthesized in stereoisomerically pure form or has to be purified after the synthesis so as to be in the required stereoisomerically pure form.

One known process for synthesizing (−)-menthol is to firstly purify isopulegol so as to obtain enantiomerically pure or at least enantiomerically enriched L-(−)-isopulegol and then secondly to hydrogenate the L-(−)-isopulegol to (−)-menthol. Often, L-(−)-isopulegol is purified by means of crystallization. Crystallization is beside distillation and extraction one of the most important industrial processes for separating and purifying a substance from a mixture, in which the substance to be purified is contained in a high, medium or even low concentration. More specifically, solid crystals enriched in the substance to be separated and purified form during crystallization from a solution or melt, provided that the substance to be separated and purified has in pure form a lower solubility than the mixture of this substance with the other substances included in the solution or the substance to be separated and purified has in pure form a higher freezing temperature than the mixture of this substance with the other substances included in the melt, respectively. Usually, melt crystallization processes are subdivided in layer melt crystallization and in suspension melt crystallization. During suspension melt crystallization a melt including at least two different compounds is cooled in a vessel so that crystals are formed resulting in a suspension of crystalline particles, which are enriched in the substance to be purified and which are dispersed in the melt depleted of the substance to be purified. After completion of the crystallization, the crystals are separated from the melt and, if necessary, further purified, such as in a second crystallization step or by means of another purification method. In contrast to this, during layer melt crystallization crystals grow on a cooled wall surface, wherein the generated crystallization heat is conveyed through the crystal layers. Due to this, the crystals are cooler than the melt in a layer crystallization method, whereas the crystals have at least substantially the same temperature as the melt in a suspension crystallization method. On account of this reason, a temperature gradient is generated between the crystal layer and the melt during a layer melt crystallization method, wherein this temperature gradient is the driving force for the crystallization. Layer melt crystallization processes are of particular industrial importance. At present, two general kinds of layer melt crystallization are known, one of which is static crystallization. During the static crystallization, the liquid phase is not moved and thus the crystals are formed and grown in a static liquid phase. More specifically, a typical static crystallizer comprises a plurality of walls, such as plates, or tubes or finned tubes which can be cooled and heated by circulating a heat transfer medium through the interior of the plates. At the beginning, the static crystallizer is filled with liquid feed mixture including the substance to be separated and purified in a certain concentration together with one or more other (undesired) substances so that the plates contact the liquid feed mixture. Then, the plates of the static crystallization vessel are cooled to a temperature below the equilibrium freezing temperature of the liquid feed mixture so that crystals enriched in the substance to be separated and purified are formed and deposited on the cooled outer surfaces of the plates. As a consequence of the deposition of the substance to be separated and purified on the cooled outer surfaces of the plates, a melt is formed from the liquid feed mixture, which has a lower concentration of the substance to be separated and purified than the liquid feed mixture. The crystallization is conducted as long as necessary to separate the desired amount of substance to be separated and purified from the melt. After completion of the crystallization, the melt is completely removed from the crystallization vessel, the cooling of the plates is terminated and optionally the plates are heated so that the crystal layers formed on the outer surfaces of the plates melt, before the melt is removed from the crystallization vessel in order to obtain the separated and purified substance. In order to increase the purity of the target product the crystal layers may be sweated by gently heating them to a temperature close to the melting temperature of the purified substance in order to partially melt the crystals, before melting them.

U.S. Pat. No. 7,868,211 B2 for instance discloses a process for purifying a crude mixture of isopulegol by crystallization, which may be performed for instance as dynamic layer crystallization or as suspension crystallization. The crude melt applied in the crystallization may comprise at least 70% by weight of isopulegol including different isopulegol stereoisomers, wherein during the crystallization stereoisomerically enriched L-(–)-isopulegol is crystallized. Even if this process allows to obtain enantiomerically enriched L-(–)-isopulegol, the separation efficiency and capacity of this process is not satisfying.

In view of this, the object underlying the present invention is to provide a process for purifying a crude composition including a monoterpene compound selected from the group consisting of monocyclic monoterpene alcohols, monocyclic monoterpene ketones, bicyclic epoxy monoterpenes and mixtures of two or more of the aforementioned compounds and in particular including a monocyclic monoterpene alcohol, which has an improved stereoisomeric separation efficiency so as to obtain a specific stereoisomer of the monoterpene compound in a high stereoisomerical purity, and which has an increased capacity or crystallization efficiency, respectively, so that the process leads to a high yield as well as high stereoisomerical purity of the target substance, wherein the process is moreover cost efficient, energy efficient and requires comparable small plants.

In accordance with the present invention this object is satisfied by providing a process for purifying a crude composition including a monoterpene compound selected from the group consisting of monocyclic monoterpene alcohols, monocyclic monoterpene ketones, bicyclic epoxy monoterpenes and mixtures of two or more of the aforementioned compounds, wherein the process comprises the step of performing a layer crystallization with a melt of the crude composition, wherein the melt of the crude composition, which is subjected to the layer crystallization, includes oxygen-containing solvent in a concentration of 20 ppm to 2% by weight, wherein the oxygen-containing solvent is selected from the group consisting of water, $C_{1-6}$-alcohols, $C_{1-6}$-carboxylic acids, $C_{1-6}$-ketones, $C_{1-6}$-aldehydes, $C_{1-12}$-ethers, $C_{1-12}$-esters and mixtures of two or more of the aforementioned solvents.

This invention bases on the surprising finding that by performing a layer melt crystallization of a crude composition including a monoterpene compound selected from the group consisting of monocyclic monoterpene alcohols, monocyclic monoterpene ketones, bicyclic epoxy monoterpenes and mixtures of two or more of the aforementioned compounds and particularly that by performing a layer melt crystallization of a crude monocyclic monoterpene alcohol including composition, to which a specific oxygen-containing solvent is added in a specific amount, namely to which an oxygen-containing solvent selected from the group consisting of water, $C_{1-6}$-alcohols, $C_{1-6}$-carboxylic acids, $C_{1-6}$-ketones, $C_{1-6}$-aldehydes, $C_{1-12}$-ethers, $C_{1-12}$-esters and mixtures of two or more of the aforementioned solvents is added in an amount so that the concentration of oxygen-containing solvent in the crude mixture being crystallized is 20 ppm to 2% by weight, not only the stereoisomeric separation efficiency is improved, but also the capacity or crystallization efficiency, respectively, is significantly increased so that the target stereoisomer of the monoterpene compound is obtained in a high yield and in a stereoisomerically high purity. Moreover, it is assumed that by adding the specific amount of the specific oxygen-containing solvent to the crude composition, the formation of a metastable phase of the monoterpene compound is favored. Monoterpene compounds selected from the group consisting of monocyclic monoterpene alcohols, monocyclic monoterpene ketones, bicyclic epoxy monoterpenes and mixtures of two or more of the aforementioned compounds, which may be polymorphous, such as for example monocyclic monoterpene alcohols and in particular isopulegol, crystallize in different crystal modifications at different temperatures, wherein the metastable phase(s) melt(s) at significantly lower temperatures than the stable phase(s). By favoring the formation of the metastable phase of the monoterpene compound during the crystallization, the separation efficiency as well as the drainage performance of the first sweating fraction can be significantly improved. All in all, the process in accordance with the present invention leads to a high yield as well as stereoisomerically high purity of the target substance, wherein the process is furthermore cost efficient, energy efficient and requires comparable small plants.

Purifying a crude composition including a monoterpene compound selected from the group consisting of monocyclic monoterpene alcohols, monocyclic monoterpene ketones, bicyclic epoxy monoterpenes and mixtures of two or more of the aforementioned compounds means in accordance with the present invention that the concentration of the monoterpene compound in the crystallized product is increased in comparison to the concentration of the monoterpene compound in the crude composition and/or that the concentration of one or more stereoisomers of the monoterpene compound in the crystallized product is increased in comparison to the concentration of the respective stereoisomer(s) of the monoterpene compound in the crude composition. Thus, the term purifying a crude composition including a monoterpene compound particularly comprises the stereoisomeric separation, such as enantiomeric separation, of a monoterpene compound and particularly of a monocyclic monoterpene alcohol and thus also comprises the case that the concentration of one or more stereoisomers of the monoterpene compound in the crystallized product is increased in comparison to the concentration of the respective stereoisomer(s) of the compound monoterpene in the crude composition, even if the concentration of the monoterpene compound itself in the crystallized product is lower than that of the monoterpene compound in the crude composition.

Concerning the monoterpene compound selected from the group consisting of monocyclic monoterpene alcohols, monocyclic monoterpene ketones, bicyclic epoxy monoterpenes and mixtures of two or more of the aforementioned compounds, the present invention is not particularly limited. Thus, the process in accordance with the present invention may be used for purifying a crude composition including a monoterpene compound, such as a compound selected from the group consisting of isopulegol, menthol, alpha-terpineol, thymol, carvacrol, piperitenol, perillyl alcohol, 1,4-cineol, 1,8-cineol, carvone and mixtures of two or more of the aforementioned compounds. Preferably, the monoterpene compound is selected from the group consisting of isopulegol, menthol, alpha-terpineol, thymol, carvacrol, 1,8-cineol, carvone and mixtures of two or more of the aforementioned compounds. Even more preferably, the monoterpene compound is preferably isopulegol, 1,8-cineol and/or carvone, and most preferably isopulegol.

The present invention is particularly suitable for purifying a crude composition including a monocyclic monoterpene alcohol, such as a monocyclic monoterpene alcohol selected from the group consisting of isopulegol, menthol, alpha-terpineol, thymol, carvacrol, piperitenol, perillyl alcohol and mixtures of two or more of the aforementioned monocyclic monoterpene alcohols. In particular, the process of the present invention is suitable for purifying a crude composition including several stereoisomers of a monocyclic monoterpene alcohol. Good results are in particular obtained for purifying a crude composition including as monocyclic monoterpene alcohol isopulegol, menthol, alpha-terpineol, thymol or carvacrol. More preferably, the process in accordance with the present invention is used for purifying a crude composition including isopulegol and/or menthol.

Even more preferably, the present invention is related to a process for purifying a crude composition including isopulegol. In this preferred embodiment, the crude composition may include a mixture containing two or more of any of the eight stereoisomers of isopulegol, namely L-(−)-isopulegol, D-(−)-isopulegol, L-(+)-isopulegol, D-(+)-isopulegol, L-(−)-iso-isopulegol, D-(−)-iso-isopulegol, L-(+)-iso-isopulegol, D-(+)-iso-isopulegol, L-(−)-neo-isopulegol, D-(−)-neo-isopulegol, L-(+)-neo-isopulegol, D-(+)-neo-isopulegol. L-(−)-neoiso-isopulegol, D-(−)-neoiso-isopulegol, L-(+)-neoiso-isopulegol and D-(+)-neoiso-isopulegol. More preferably, the crude composition includes at least L-(−)-isopulegol and D-(−)isopulegol and optionally one or more of the other stereoisomers of isopulegol.

Also concerning the concentration of the monoterpene compound selected from the group consisting of monocyclic monoterpene alcohols, monocyclic monoterpene ketones, bicyclic epoxy monoterpenes and mixtures of two or more of the aforementioned compounds and particularly of the monocyclic monoterpene alcohol, the crude composition is not particularly limited. For example, the crude composition may contain the monoterpene compound and preferably the monocyclic monoterpene alcohol, such as a mixture of two or more stereoisomers of a monocyclic monoterpene alcohol, in a concentration of at least 50% by weight based on the total weight of the crude composition. The concentration of the monoterpene compound means the sum of the concentrations of all stereoisomers of the monoterpene compound included in the crude composition. For the sake of completeness, it is noted that the aforementioned concentration is referred to the crude mixture as present at the start of the crystallization and thus to the melt of the crude composition as present at the start of the crystallization. More preferably, the crude composition contains the monoterpene compound and preferably the monocyclic monoterpene alcohol in a concentration of at least 70% by weight, even more preferably of at least 85% by weight and most preferably of at least 90% by weight, such as between 90% by weight and less than 100% by weight. The content of the stereoisomers of the monoterpene compound may be readily determined by conventional methods, such as in particular by chromatographic methods, such as preferably gas chromatography.

In the preferred embodiment of the present invention, in which the monoterpene compound is isopulegol, the concentration of the isopulegol in the crude composition is at least 50% by weight, more preferably at least 70% by weight, even more preferably at least 85% by weight and most preferably at least 90% by weight, such as between 90% by weight and less than 100% by weight.

In the particular preferred embodiment of the present invention, in which the crude composition contains an isopulegol mixture of at least L-(−)-isopulegol and D-(−)-isopulegol and optionally one or more of the other stereoisomers of isopulegol, the content of the L-(−)n-isopulegol in the isopulegol mixture is preferably more than 70% by weight, more preferably more than 85% by weight and most preferably more than 92% by weight. Consequently, if the total concentration of isopulegol in the crude mixture is 90% by weight, the content of the L-(−)-n-isopulegol in the crude composition is preferably more than 70%×90%=63% by weight, more preferably more than 85%×90%=76.5% by weight and most preferably more than 92%×90%=82.80% by weight. The enantiomeric excess (ee) is defined as (content of L stereoisomer−content of D stereoisomer)/(content of L stereoisomer+content of D stereoisomer)* 100%. Thus, the ee-value is preferably more than 63, more preferably more than 76.5 and most preferably more than 82.80.

In accordance with the present invention, any oxygen-containing solvent selected from the group consisting of water, $C_{1-6}$-alcohols, $C_{1-6}$-carboxylic acids, $C_{1-6}$-ketones, $C_{1-6}$-aldehydes, $C_{1-12}$-ethers, $C_{1-12}$-esters and mixtures of two or more of the aforementioned solvents may be applied. Good results are in particular obtained, when the oxygen-containing solvent is selected from the group consisting of water, $C_{1-4}$-alcohols, $C_{1-4}$-carboxylic acids, $C_{1-4}$-ketones, $C_{1-4}$-aldehydes, $C_{1-6}$-ethers, $C_{1-6}$-esters and mixtures of two or more of the aforementioned solvents. More preferably, the oxygen-containing solvent is selected from the group consisting of water, methanol, ethanol, iso-propanol, n-propanol, 1-butanol, 2-butanol, formic acid, acetic acid, acetone, formaldehyde and mixtures of two or more of the aforementioned solvents. Even more preferably, the oxygen-containing solvent is selected from the group consisting of water, methanol, ethanol, iso-propanol, n-propanol, 1-butanol, 2-butanol and mixtures of two or more of the aforementioned solvents. Still further preferably, the oxygen-containing solvent is selected from the group consisting of water, methanol and mixtures of water and methanol. Most preferably, the oxygen-containing solvent is water. The oxygen-containing solvent, in particular water, may be added to the crude composition before subjecting it to the layer crystallization, or, alternatively, may be included in the crude composition from a prior distillation step.

In accordance with a preferred embodiment of the present invention, the oxygen-containing solvent is no acetone and the melt of the crude composition, which is subjected to layer crystallization, does not contain acetone.

In a further development of the idea of the present invention it is suggested that the crude composition includes as monoterpene compound at least L-(−)-isopulegol and D-(−)isopulegol and optionally one or more of the other stereoisomers of isopulegol and as oxygen-containing solvent water, methanol or a mixture of water and methanol. Most preferably, the crude composition includes as monoterpene compound at least L-(−)-isopulegol and D-(−)-isopulegol and optionally one or more of the other stereoisomers of isopulegol and as oxygen-containing solvent water.

The oxygen-containing solvent, which is most preferably water, is added to the crude composition before the start of the layer crystallization.

In accordance with the present invention, the crude composition contains 20 ppm to 2% by weight of the oxygen-containing solvent. Particular good results are obtained, when the melt of the crude composition, which is subjected to the layer crystallization, includes 50 ppm to 1.5% by weight, still preferably 100 ppm to 1.5% by weight, more preferably 500 ppm to 1% by weight and most preferably 0.1 to 0.5% by weight of the oxygen-containing solvent. Particularly preferred is a process for purifying a crude composition including a monoterpene compound selected from the group consisting of monocyclic monoterpene alcohols, monocyclic monoterpene ketones, bicyclic epoxy monoterpenes and mixtures of two or more of the aforementioned compounds, wherein the crude composition includes as monoterpene compound at least L-(−)-isopulegol and D-(−)-isopulegol and optionally one or more of the other stereoisomers of isopulegol and as oxygen-containing solvent 500 ppm to 1% by weight water and/or methanol and most preferably 0.1 to 0.5% by weight water. The content of the solvent may be readily determined by conventional methods, such as for alcohol (e.g. methanol and ethanol) in particular by chromatographic methods, such as preferably gas chromatography. The content of water is determined according to the present invention by volumetric or coulometric Karl Fischer titrators.

Concerning the kind of layer crystallization, the present invention is not particularly limited. However, particular good results are obtained, when the layer crystallization is a static crystallization. More specifically, the layer crystallization is preferably performed in a static crystallizer, which comprises a plurality of walls, such as plates or tubes or finned tubes, which can be cooled and heated by circulating a heat transfer medium through the interior of the plates.

In order to even improve the yield of the target stereoisomer of the monoterpene compound selected from the group consisting of monocyclic monoterpene alcohols, monocyclic monoterpene ketones, bicyclic epoxy monoterpenes and mixtures of two or more of the aforementioned compounds and in particular of the monocyclic monoterpene alcohol, it is suggested in a further development of the present invention that the process additionally comprises a priming step comprising the wetting of plates of the static crystallizer with a monoterpene compound and particularly with a monocyclic monoterpene alcohol, which corresponds to that to be purified. Preferably, the monoterpene compound used in the priming step has a purity of at least than 70% by weight, more preferably of at least 85% by weight, even more preferably of at least 92% by weight and most preferably of at least 99% by weight, such as in particular of about 100% by weight. Thus, in the particular preferred embodiment of the present invention, in which the crude composition includes as monoterpene compound isopulegol and most preferably a mixture including at least L-(−)-isopulegol and D-(−)-isopulegol and optionally one or more of the other stereoisomers of isopulegol, the priming step comprises wetting of plates of the crystallizer with a composition containing at least 70% by weight L-(−)-n-isopulegol, more preferably at least 85% by weight L-(−)-n-isopulegol, even more preferably at least 92% by weight L-(−)-n-isopulegol and most preferably at least 99% by weight, such as about 100% by weight, L-(−)-n-isopulegol. Also in this embodiment it is preferred that the crude composition includes as oxygen-containing solvent 500 ppm to 1% by weight water and/or methanol and most preferably 0.1 to 0.5% by weight water. The content of the monoterpene compound may be readily determined by conventional methods, such as in particular by chromatographic methods, such as preferably gas chromatography.

In a further development of the idea of the present invention it is suggested that the layer crystallization of the process in accordance with the present invention comprises 1 to 10, more preferably 2 to 6, still more preferably 3 to 5 and most preferably 4 crystallization stages.

The temperature at which the layer crystallization takes place is—in particular in the case, in which the monoterpene compound is isopulegol and preferably a mixture including at least L-(−)-isopulegol and D-(−)-isopulegol and optionally one or more of the other stereoisomers of isopulegol—preferably more than 0 to 25° C., more preferably 5 to 20° C. and most preferably 11 to 15° C. The crystallization time for any crystallization stage is preferably between 10 and 100 hours, more preferably between 15 and 50 hours and most preferably between 20 and 40 hours.

In the case that the layer crystallization of the process in accordance with the present invention comprises more than one crystallization stage, it is preferred that the process comprises after the first crystallization stage the step of adding oxygen-containing solvent to at least one of the fractions to be crystallized in one or more of the further crystallization stages. The reason therefore is that the mother liquor is depleted during any crystallization stage of oxygen-containing solvent, because about 40% of the oxygen-containing solvent contained in the crude melt at the beginning of the crystallization stage is incorporated during the crystallization stage into the crystal layer(s), whereas about 60% of the oxygen-containing solvent contained in the crude melt at the beginning of the crystallization stage remains in the mother liquor. The amount of the added oxygen-containing solvent is adjusted so that the concentration of the oxygen-containing solvent after the addition is in the crude composition between 20 ppm and 2% by weight, still preferably 50 ppm to 1.5% by weight, still preferably between 100 ppm and 1.5% by weight, more preferably between 500 ppm and 1% by weight and most preferably between 0.1 and 0.5% by weight.

In accordance with still a further preferred embodiment of the present invention, the oxygen-containing solvent is added to the at least one fraction to be crystallized in one or more of the further crystallization stages between before any of the second to before the final crystallization stage. The amount of the added oxygen-containing solvent is adjusted so that the concentration of the oxygen-containing solvent after the addition is in the crude composition between 20 ppm and 2% by weight, preferably 50 ppm to 1.5% by weight, still preferably between 100 ppm and 1.5% by weight, more preferably between 500 ppm and 1% by weight and most preferably between 0.1 and 0.5% by weight.

Most preferably, after each crystallization stage and before the next crystallization stage oxygen-containing solvent is added to the fraction to be crystallized in the next crystallization stage in an amount so that the concentration of the oxygen-containing solvent after the addition is in the crude composition between 20 ppm and 2% by weight, preferably 50 ppm to 1.5% by weight, still preferably between 100 ppm and 1.5% by weight, more preferably between 500 ppm and 1% by weight and most preferably between 0.1 and 0.5% by weight.

In accordance with a further particular preferred embodiment of the present invention it is suggested that the crude composition contains isopulegol—preferably a mixture including at least L-(−)-isopulegol and D-(−)-isopulegol and optionally one or more of the other stereoisomers of isopulegol—as monocyclic monoterpene alcohol, wherein with the process a first product stream and a second product stream are produced. While the first product stream—which is obtained from the crystallized fraction(s) of the crystallization stage(s)—is an enriched L-(−)-n-isopulegol fraction with a purity of L-(−)-n-isopulegol of at least 98% by weight, more preferably of at least 99% by weight, even more preferably of at least 99.5% by weight and most preferably of at least 99.9% by weight (i.e. an ee-value of preferably at least 96, more preferably of at least 98, even more preferably of at least 99 and most preferably of 99.8), the second product stream—which is the remaining melt or mother liquor, respectively, after the crystallization stage(s)—is a racemic mixture of L-(−)-n-isopulegol and D-(−)-n-isopulegol, in which preferably the content of the L-(−)-n-isopulegol in the mixture is more than 50% by weight but less than 65% by weight, more preferably less than 60% by weight and most preferably less than 55% by weight. More specifically, the enantiomeric excess of one of the stereoisomers in the racemic mixture is preferably less than 10%, more preferably less than 5%, still more preferably less than 1%. A purity of L-(−)-n-isopulegol of at least 98% by weight means in this context that the first product stream includes, based on the total content of isopulegol, at least 98% by weight L-(−)-n-isopulegol. Preferably, the absolute content of L-(−)-n-isopulegol in the first product stream is at least 98% by weight, more preferably of at least 99% by weight and most preferably of at least 99.5% by weight.

Likewise, if the monoterpene compound is different from isopulegol, the process in accordance with the present invention leads for so-called conglomerate forming groups to a first and a second product stream, wherein the first product stream—which is obtained from the crystallized fraction(s)—is an enriched monoterpene compound fraction with a purity of a specific stereoisomer of the monoterpene compound of at least 98% by weight, more preferably of at least 99% by weight, even more preferably of at least 99.5% by weight and most preferably of at least 99.9% by weight, the second product stream—which is the remaining melt or mother liquor, respectively, after the crystallization stage(s)—is a racemic mixture of this stereoisomer and at least another stereoisomer of the monoterpene compound, in which preferably the content of this stereoisomer in the mixture is more than 50% by weight but less than 65% by weight, more preferably less than 60% by weight and most preferably less than 55% by weight.

As set out above, while the second product stream is the mother liquor discharged from the crystallizer of the last crystallization stage, the first product stream is composed of the crystallized fraction(s) of a respective crystallization stage, wherein the crystallized fraction(s) is/are obtained by melting the fraction(s) crystallized on the cooled surface(s) of the crystallizer.

In order to increase the purity of the target product, it is preferable to perform in any of the crystallization stages at least one sweating step before melting the fraction(s) crystallized on the cooled surface(s) of the crystallizer. Sweating means that the crystal layer(s) deposited on the cooled surface(s) is/are gently heated to a temperature close to the melting temperature of the purified substance in order to partially melt the crystals. Trapped and adherent melt, which contains the impurities, drains off during the partial melting of the crystals and is then removed from the crystallization zone. In order to conduct such a sweating, the surface, on which the crystals are deposited, is heated with a heat transfer medium to the desired temperature. Therefore, it is necessary to completely remove the mother liquid or at least substantially all of the mother liquid before the sweating step. The sweating may be performed for one or several times before melting the crystal layer(s) deposited on the cooled surface(s).

In accordance with a particular preferred embodiment of the present invention, the crude composition contains a mixture of L-(−)-n-isopulegol and D-(−)-n-isopulegol as monoterpene compound and the process comprises the following steps:

a) melting the crude composition.
b) adding water and/or methanol as oxygen-containing solvent to the crude composition so that the concentration of the oxygen-containing solvent in the melt is 20 ppm to 2% by weight, preferably 50 ppm to 1.5% by weight, still preferably 100 ppm to 1.5% by weight, more preferably 500 ppm to 1% by weight and most preferably 0.1 to 0.5% by weight,
c) subjecting the melt obtained in step b) to a first static layer melt crystallization stage in a static crystallizer,
d) after the crystallization of step c), removing the remaining melt (or mother liquor, respectively) as a first residue fraction from the static crystallizer used in step c), melting the crystal layer deposited during the first crystallization stage in the static crystallizer to obtain a first crystallized fraction and subjecting the first crystallized fraction to a second static layer melt crystallization stage in a static crystallizer,
e) after the crystallization of step d), removing the remaining melt (or mother liquor, respectively) as a second residue fraction from the static crystallizer, melting the crystal layer deposited during the second crystallization stage in the static crystallizer used in step d) to obtain as a second crystallized fraction a first product stream of enriched L-(−)-n-isopulegol having a purity of at least 98% by weight, more preferably of at least 99% by weight, even more preferably of at least 99.5% by weight and most preferably of at least 99.9% by weight,
f) subjecting the remaining melt discharged as the first residue fraction from the static crystallizer used in step c) to a third static layer melt crystallization stage in a static crystallizer,
g) after the crystallization of step f), removing the remaining melt as a third residue fraction from the static crystallizer, melting the crystal layer deposited during the third crystallization stage in the static crystallizer used in step f) to obtain a third crystallized fraction and subjecting the remaining melt discharged from the static crystallizer used in step f) as the third residue fraction to a fourth static layer melt crystallization stage in a static crystallizer, h) after the crystallization of step g), removing the remaining melt as a fourth residue fraction from the static crystallizer to obtain a second product stream of a racemic mixture of L-(−)-n-isopulegol and D-(−)-n-isopulegol, wherein preferably the content of the L-(−)-n-isopulegol in the mixture is more than 50% by weight but less than 65% by weight, more preferably less than 60% by weight and most preferably less than 55% by weight, and melting the crystal layer deposited during the fourth crystallization stage in the static crystallizer used in step g) to obtain a fourth crystallized fraction.

In a refinement of the aforementioned embodiment it is suggested that the process further comprises one or more of the following steps:
i) feeding the remaining melt discharged as the second residue fraction from the static crystallizer used in step d) to the static crystallizer of the first static layer melt crystallization stage,
ii) feeding the third crystallized fraction to the static crystallizer of the first static layer melt crystallization stage,
iii) feeding the fourth crystallized fraction to the static crystallizer of the third static layer melt crystallization stage.

Furthermore, it is preferred that the process in accordance with the aforementioned embodiment of the present invention further comprises one or more of the following steps:
iv) before melting in step d) the crystal layer deposited during the first crystallization stage, carrying out a sweating of the crystal layer and preferably feeding a first portion of the sweating fraction obtained thereby to the first residue fraction and feeding a second portion of the sweating fraction obtained thereby to the static crystallizer of the first static layer melt crystallization stage,
v) before melting in step e) the crystal layer deposited during the second crystallization stage, carrying out a sweating of the crystal layer and preferably feeding a first portion of the sweating fraction obtained thereby to the second residue fraction and feeding a second portion of the sweating fraction obtained thereby to the static crystallizer of the second static layer melt crystallization stage,
vi) before melting in step g) the crystal layer deposited during the third crystallization stage, carrying out a sweating of the crystal layer and preferably feeding a first portion of the sweating fraction obtained thereby to the third residue fraction and feeding a second portion of the sweating fraction obtained thereby to the static crystallizer of the third static layer melt crystallization stage,
vii) before melting in step h) the crystal layer deposited during the fourth crystallization stage, carrying out a sweating of the crystal layer and preferably feeding a first portion of the sweating fraction obtained thereby to the second product stream obtained as fourth residue fraction and feeding a second portion of the sweating fraction obtained thereby to the static crystallizer of the fourth static layer melt crystallization stage.

According to another aspect, the present invention relates to an enriched composition of a monoterpene compound selected from the group consisting of monocyclic monoterpene alcohols, monocyclic monoterpene ketones, bicyclic epoxy monoterpenes and mixtures of two or more of the aforementioned compounds obtainable with the aforementioned process, which includes at least 98% by weight, preferably at least 98.5% by weight, more preferably at least 99% by weight, even more preferably at least 99.5% by weight and most preferably at least 99.9% by weight of monoterpene compound and 20 ppm to 2% by weight, preferably 50 ppm to 1.5% by weight, still preferably 100 ppm to 1.5% by weight, more preferably 500 ppm to 1% by weight and most preferably 0.1 to 0.5% by weight of oxygen-containing solvent. In particular, the present invention relates to an enriched monocyclic monoterpene alcohol composition obtainable with the aforementioned process, which includes at least 98% by weight, preferably at least 98.5% by weight, more preferably at least 99% by weight, even more preferably at least 99.5% by weight and most preferably at least 99.9% by weight of monocyclic monoterpene alcohol and 20 ppm to 2% by weight, preferably 50 ppm to 1.5% by weight, still preferably 100 ppm to 1.5% by weight, more preferably 500 ppm to 1% by weight and most preferably 0.1 to 0.5% by weight of oxygen-containing solvent, wherein the oxygen-containing solvent is preferably no acetone and wherein the enriched composition preferably does not contain acetone.

The total content of impurities in the enriched composition. i.e. the total content of all compounds except the monoterpene compound and the oxygen-containing solvent, is preferably less than 1% by weight, more preferably less than 0.5% by weight, still more preferably not more than 0.3% by weight, even more preferably not more than 0.2% by weight and most preferably not more than 0.1% by weight. Examples for impurities, in particular if the monoterpene compound is isopulegol, are isopulegon, neomenthon, L-menthol, pulegon, phenylcyclohexan and others.

Preferably, the monocyclic monoterpene alcohol is isopulegol and the enriched composition includes at least 98% by weight, preferably at least 99% by weight, even more preferably at least 99.5 and most preferably at least 99.9% by weight of L-(−)-n-isopulegol and 20 ppm to 2% by weight, preferably 50 ppm to 1.5% by weight, still preferably 100 ppm to 1.5% by weight, more preferably 500 ppm to 1% by weight and most preferably 0.1 to 0.5% by weight of water and/or methanol. This corresponds to the first product stream described above in connection with the particular preferred embodiment of the present invention.

In addition, the present invention relates to a racemic mixture of L-(−)-n-isopulegol and D-(−)-n-isopulegol, preferably with a content of the L-(−)-n-isopulegol in the mixture of more than 50% by weight but less than 65% by weight, more preferably less than 60% by weight and most preferably less than 55% by weight and with a content of water and/or methanol of 20 ppm to 2% by weight, preferably of 50 ppm to 1.5% by weight, still preferably of 100 ppm to 1.5% by weight, more preferably of 500 ppm to 1% by weight and most preferably 0.1 to 0.5% by weight. This corresponds to the second product stream described above in connection with the particular preferred embodiment of the present invention.

Moreover, the present invention is related to the use of the aforementioned process for producing an optically active, essentially enantiomerically and diastereoisomerically pure L-menthol and/or racemic menthol by hydrogenating the L-(−)-n-isopulegol obtained with the process.

In accordance with another aspect, the present invention relates to the use of the aforementioned enriched composition for preparing an optically active, essentially enantiomerically and diastereoisomerically pure L-menthol by hydrogenating the L-(−)-n-isopulegol.

In accordance with still another aspect, the present invention relates to the use of the aforementioned racemic melt mixture of L-(−)-n-isopulegol and D-(−)-n-isopulegol to prepare racemic menthol by hydrogenating the racemic mixture.

BRIEF DESCRIPTION OF THE DRAWING

The invention will be explained in more detail hereinafter with reference to the drawings.

FIG. 1 schematically shows a scheme of the process in accordance with one embodiment of the present invention.

DETAILED DESCRIPTION

The sole FIG. 1 schematically shows a scheme of the process in accordance with one embodiment of the present invention. More specifically, the process shown in FIG. 1 comprises four crystallization stages 10, 12, 14 and 16.

As feed, melt of crude composition 18 is introduced as feed into the first crystallization stage 10. The melt of crude composition 18 of this embodiment includes 90% by weight of a mixture of L-(−)-n-isopulegol and D-(−)-n-isopulegol, 0.5% by weight of water, which was previously added to the mixture, and remainder to 100% by weight further stereoisomers of isopulegol and impurities from the synthesis of the isopulegol. The isopulegol mixture contained in the melt of crude composition 18 includes about 90% by weight of L-(−)-n-isopulegol and about 10% by weight of D-(−)-n-isopulegol. The feed is crystallized in the crystallizer of the first crystallization stage 10 for about 26 hours (including the sweating, melting and draining of the fractions) at a temperature of for example about 10° C. The melting temperature depends on the composition, i.e. on the amount of impurities, and can be significantly lower than 13° C., which is the melting temperature of pure L-(−)-n-isopulegol. One skilled in the art will understand that the temperature will decrease progressively with the stages, i.e., with increasing concentration of impurities. During the crystallization, L-(−)n-isopulegol crystallizes together with a part of the water on the cooled surface of the crystallizer, whereas a racemate of L-(−)-n-isopulegol and D-(−)-n-isopulegol together with remaining impurities and water remain as mother liquor as melt. After termination of the crystallization in the crystallizer of the first crystallization stage 10, the mother liquor or remaining melt, respectively, is discharged as first residue fraction 26 from the crystallizer. Thereafter, the crystal layer deposited during the first crystallization stage 10, is subjected to a sweating step, wherein the first portion of the sweating fraction (not shown) obtained thereby is added to the first residue fraction 26 and the second portion of the first sweating fraction 22 obtained thereby is combined, as described above, with the crude composition 18, before incorporating the feed into the crystallizer of the first crystallization stage 10. Afterwards, the crystal layer deposited during the first crystallization stage 10 in the crystallizer is melted so as to obtain a first crystallized fraction 28 of the purified L-(−)-n-isopulegol.

The first crystallized fraction 28 is fed together with the second portion of the second sweating fraction 30, after having been collected in tanks for intermediate storage, into the second crystallization stage 12. The feed is crystallized in the crystallizer of the second crystallization stage 12 for about 34 hours (including the sweating, melting and draining of the fractions) at a temperature of about 12° C. During the crystallization, L-(−)-n-isopulegol crystallizes together with a part of the water on the cooled surface of the crystallizer, whereas a racemate of L-(−)-n-isopulegol and D-(−)-n-isopulegol together with remaining impurities and water remain as mother liquor as melt. After termination of the crystallization in the crystallizer of the second crystallization stage 12, the mother liquor or remaining melt, respectively, is discharged as second residue fraction 24 from the crystallizer. Thereafter, the crystal layer deposited during second crystallization stage 12 is subjected to a sweating step, whereas the first portion of the second sweating fraction (not shown) obtained thereby is added to the second residue fraction 24 and the second portion of the second sweating fraction 30 obtained thereby is combined, as described above, with the first crystallized fraction 28. Afterwards, the crystal layer deposited during the second crystallization stage 12 in the crystallizer is melted so as to obtain as second crystallized fraction 32 the first product stream 32 of pure L-(−)-n-isopulegol containing about 99.7% by weight L-(−)-n-isopulegol and about 0.3% by weight water and possible impurities.

The first residue fraction 26 is fed together with the second portion of the third sweating fraction 34 and the fourth crystallized fraction 36 into the third crystallization stage 14. The feed is crystallized in the crystallizer of the third crystallization stage 14 for about 39 hours (including the sweating, melting and draining of the fractions) at a temperature of about 4° C. During the crystallization, L-(−)-n-isopulegol crystallizes together with a part of the water on the cooled surface of the crystallizer, whereas a racemate of L-(−)-n-isopulegol and D-(−)-n-isopulegol together with remaining impurities and water remain as mother liquor as melt. After termination of the crystallization in the crystallizer of the third crystallization stage 14, the mother liquor or remaining melt, respectively, is discharged as third residue fraction 38 from the crystallizer. Thereafter, the crystal layer deposited during the third crystallization stage 14 is subjected to a sweating step, wherein the first portion of the third sweating fraction (not shown) obtained thereby is added to the third residue fraction 38 and the second portion of the third sweating fraction 34 obtained thereby is, as described above, combined with the fourth crystallized fraction 36. Afterwards, the crystal layer deposited during the third crystallization stage 14 in the crystallizer is melted so as to obtain a third crystallized fraction 20 of purified L-(−)-n-isopulegol.

The third residue fraction 38 is fed together with the second portion of the fourth sweating fraction 40 into the fourth crystallization stage 16. The feed is crystallized in the crystallizer of the fourth crystallization stage 16 for about 70 hours (including the sweating, melting and draining of the fractions) at a temperature of about −7° C. During the crystallization, L-(−)-n-isopulegol crystallizes together with a part of the water on the cooled surface of the crystallizer, whereas a racemate of L-(−)-n-isopulegol and D-(−)-n-isopulegol together with remaining impurities and water remain as mother liquor as melt. After termination of the crystallization in the crystallizer of the fourth crystallization stage 16, the mother liquor or remaining melt, respectively, is discharged as fourth residue fraction 42 as second product stream 42 of racemate of L-(−)-n-isopulegol and D-(−)-n-isopulegol with an enantiomer excess of less than 5% from the crystallizer. Thereafter, the crystal layer deposited during the fourth crystallization stage 16 is subjected to a sweating step, wherein the first portion of the fourth sweating fraction (not shown) obtained thereby is added to the fourth residue fraction or second product stream 42, respectively, and the second portion of the fourth sweating fraction 40 obtained thereby is, as described above, combined with the third residue fraction 38. Afterwards, the crystal layer deposited during the fourth crystallization stage 16 in the crystallizer is melted so as to obtain a fourth crystallized fraction 36 of purified L-(−)-n-isopulegol.

The invention claimed is:

1. A process for purifying a crude composition including a monoterpene compound selected from the group consisting of monocyclic monoterpene alcohols, monocyclic monoterpene ketones, bicyclic epoxy monoterpenes and mixtures of two or more of the aforementioned compounds, the process comprising performing a layer crystallization with a melt of the crude composition, the melt of the crude composition, which is subjected to the layer crystallization, including oxygen-containing solvent in a concentration of 20 ppm to 2% by weight, the oxygen-containing solvent selected from the group consisting of water, C1-6-alcohols, C1-6-carboxylic acids, C1-6-ketones, C1-6-aldehydes, C1-12-ethers, C1-12-esters and mixtures of two or more of the aforementioned solvents.

2. The process in accordance with claim 1, wherein the crude composition contains a compound selected from the group consisting of isopulegol, menthol, alpha-terpineol, thymol, carvacrol, piperitenol, perillyl alcohol, 1,4 cineol, 1,8-cineol, carvone and mixtures of two or more of the aforementioned compounds.

3. The process in accordance with claim 1, wherein the crude composition contains a mixture of L-(−)-n-isopulegol and D-(−)-n-isopulegol, wherein the content of the L-(−)-n-isopulegol in the mixture is more than 70% by weight.

4. The process in accordance with claim 1, wherein the solvent is selected from the group consisting of water, methanol, ethanol, iso-propanol, n propanol, 1-butanol, 2-butanol and mixtures of two or more of the aforementioned solvents.

5. The process in accordance with claim 1, wherein the melt of the crude composition, which is subjected to the layer crystallization, includes 50 ppm to 1.5% by weight of the oxygen-containing solvent.

6. The process in accordance with claim 1, wherein the process additionally comprises a priming comprising wetting of plates of the crystallizer with a monoterpene compound, which corresponds to that to be purified, having a purity of at least 70% by weight.

7. The process in accordance with claim 1, wherein the layer crystallization comprises a first crystallization stage through a tenth crystallization stage.

8. The process in accordance with claim 7, wherein after the first crystallization stage, oxygen-containing solvent is added to at least one fraction to be crystallized in one or more of the further crystallization stages.

9. The process in accordance with claim 8, wherein oxygen-containing solvent is added to the at least one fraction to be crystallized in one or more of the further crystallization stages between before any of the second to before the final crystallization stage.

10. The process in accordance with claim 1, wherein the crude composition contains isopulegol as monoterpene compound and wherein with the process a first and a second product stream are produced, wherein the first product stream is an enriched L-(−)-n-isopulegol fraction with a purity of L-(−)-n-isopulegol of at least 98% by weight.

11. The process in accordance with claim 1, wherein the crude composition contains a mixture of L-(−)-n-isopulegol and D-(−)-n-isopulegol as monoterpene compound and wherein the process comprises the following steps:

a) melting the crude composition;
b) adding water and/or methanol as oxygen-containing solvent to the crude composition so that the concentration of the oxygen-containing solvent in the melt is 20 ppm to 2% by weight;
c) subjecting the melt obtained in step b) to a first static layer melt crystallization stage in a static crystallizer;
d) after the crystallization, removing the remaining melt as a first residue fraction from the static crystallizer used in step c), melting the crystal layer deposited during the first crystallization stage in the static crystallizer to obtain a first crystallized fraction and subjecting the first crystallized fraction to a second static layer melt crystallization stage in a static crystallizer;
e) after the crystallization of step d), removing the remaining melt as a second residue fraction from the static crystallizer, melting the crystal layer deposited during the second crystallization stage in the static crystallizer used in step d) to obtain as a second crystallized fraction a first product stream of enriched L-(−)-n-isopulegol having a purity of at least 98% by weight;
f) subjecting the remaining melt discharged as the first residue fraction from the static crystallizer used in step c) to a third static layer melt crystallization stage in a static crystallizer;
g) after the crystallization of step f), removing the remaining melt as a third residue fraction from the static crystallizer, melting the crystal layer deposited during the third crystallization stage in the static crystallizer used in step f) to obtain a third crystallized fraction and subjecting the remaining melt discharged from the static crystallizer as the third residue fraction to a fourth static layer melt crystallization stage in a static crystallizer; and
h) after the crystallization of step g), removing the remaining melt as a fourth residue fraction from the static crystallizer to obtain a second product stream of a racemic mixture of L-(−)-n-isopulegol and D-(−)-n-isopulegol, and melting the crystal layer deposited during the fourth crystallization stage in the static crystallizer to obtain a fourth crystallized fraction.

12. The process in accordance with claim 11, wherein the process further comprises one or more of the following steps:

feeding the remaining melt discharged as the second residue fraction from the static crystallizer used in step d) to the static crystallizer of the first static layer melt crystallization stage;
feeding the third crystallized fraction to the static crystallizer of the first static layer melt crystallization stage; and
feeding the fourth crystallized fraction to the static crystallizer of the third static layer melt crystallization stage.

13. The process in accordance with claim 11, wherein the process further comprises one or more of the following steps:

before melting in step d) the crystal layer deposited during the first crystallization stage, carrying out a sweating of the crystal layer and feeding a first portion of the sweating fraction obtained thereby to the first residue fraction and feeding a second portion of the sweating fraction obtained thereby to the static crystallizer of the first static layer melt crystallization stage;
before melting in step e) the crystal layer deposited during the second crystallization stage, carrying out a sweating of the crystal layer and feeding a first portion of the sweating fraction obtained thereby to the second residue fraction and feeding a second portion of the sweating fraction obtained thereby to the static crystallizer of the second static layer melt crystallization stage;

before melting in step g) the crystal layer deposited during the third crystallization stage, carrying out a sweating of the crystal layer and preferably feeding a first portion of the sweating fraction obtained thereby to the third residue fraction and feeding a second portion of the sweating fraction obtained thereby to the static crystallizer of the third static layer melt crystallization stage; and before melting in step h) the crystal layer deposited during the fourth stage, carrying out a sweating of the crystal layer and feeding a first portion of the sweating fraction obtained thereby to the second product stream obtained as fourth residue fraction and feeding a second portion of the sweating fraction obtained thereby to the static crystallizer of the fourth static layer melt crystallization stage.

14. An enriched composition of a monoterpene compound selected from the group consisting of monocyclic monoterpene alcohols, monocyclic monoterpene ketones, bicyclic epoxy monoterpenes and mixtures of two or more of the aforementioned compounds, including at least 98% by weight of a monoterpene compound selected from the group consisting of monocyclic monoterpene alcohols, monocyclic monoterpene ketones, bicyclic epoxy monoterpenes and mixtures of two or more of the aforementioned compounds, and 20 ppm to 2% by weight of oxygen-containing solvent, wherein the enriched composition does not contain acetone.

15. A racemic mixture of L-(−)-n-isopulegol and D-(−)-n-isopulegol, with a content of the L-(−)-n-isopulegol in the mixture of more than 50% by weight but less than 65% by weight and with a content of water or methanol of 20 ppm to 2% by weight.

* * * * *